United States Patent
Sawada et al.

(10) Patent No.: US 10,451,987 B2
(45) Date of Patent: Oct. 22, 2019

(54) TONER, IMAGE FORMING APPARATUS, IMAGE FORMING METHOD, AND TONER ACCOMMODATING UNIT

(71) Applicants: Toyoshi Sawada, Shizuoka (JP); Kazumi Suzuki, Shizuoka (JP); Yu Naito, Shizuoka (JP)

(72) Inventors: Toyoshi Sawada, Shizuoka (JP); Kazumi Suzuki, Shizuoka (JP); Yu Naito, Shizuoka (JP)

(73) Assignee: Ricoh Company, Ltd., Tokyo (JP)

( * ) Notice: Subject to any disclaimer, the term of this patent is extended or adjusted under 35 U.S.C. 154(b) by 0 days.

(21) Appl. No.: 16/210,003

(22) Filed: Dec. 5, 2018

(65) Prior Publication Data

US 2019/0196349 A1    Jun. 27, 2019

(30) Foreign Application Priority Data

Dec. 25, 2017 (JP) ................. 2017-247915
Oct. 31, 2018 (JP) ................. 2018-205410

(51) Int. Cl.
*G03G 9/08* (2006.01)
*G03G 9/09* (2006.01)
(Continued)

(52) U.S. Cl.
CPC ........... *G03G 9/0924* (2013.01); *C07F 5/003* (2013.01); *G03G 9/09733* (2013.01);
(Continued)

(58) Field of Classification Search
CPC ........... G03G 9/09733; G03G 9/09758; G03G 9/09775
(Continued)

(56) References Cited

U.S. PATENT DOCUMENTS

2015/0030819 A1   1/2015  Naito et al.
2015/0037718 A1   2/2015  Morita et al.
(Continued)

FOREIGN PATENT DOCUMENTS

JP    2002-173622    6/2002
JP    2013-186188    9/2013
(Continued)

*Primary Examiner* — Mark A Chapman
(74) *Attorney, Agent, or Firm* — Oblon, McClelland, Maier & Neustadt, L.L.P.

(57) ABSTRACT

A toner includes a europium complex represented by the following Chemical formula Chemical formula 1

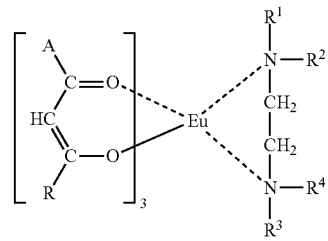

where A represents 2-naphthyl group, 2-naphthyl group having a substitution group selected from the group consisting of an alkyl group, an alkoxy group, and a halogen, R represents a fluoroalkyl group having one to three carbon atoms or a methyl group, and $R^1$, $R^2$, $R^3$, and $R^4$ each, independently represent hydrogen atoms, alkyl groups, or aryl groups, wherein the toner has a hydroxyl value of from 20 to 40 mgKOH/g.

8 Claims, 3 Drawing Sheets

(51) Int. Cl.
  *G03G 15/08*   (2006.01)
  *C07F 5/00*    (2006.01)
  *G03G 9/097*   (2006.01)

(52) U.S. Cl.
  CPC ..... *G03G 9/09758* (2013.01); *G03G 9/09775* (2013.01); *G03G 15/08* (2013.01)

(58) Field of Classification Search
  USPC .......................................... 430/108.21, 108.1
  See application file for complete search history.

(56) References Cited

U.S. PATENT DOCUMENTS

| | | |
|---|---|---|
| 2015/0072287 A1 | 3/2015 | Amemori et al. |
| 2015/0153671 A1 | 6/2015 | Yamauchi et al. |
| 2015/0212442 A1 | 7/2015 | Ishii et al. |
| 2015/0212444 A1 | 7/2015 | Yamauchi et al. |
| 2015/0220011 A1 | 8/2015 | Miyaake et al. |
| 2015/0227066 A1 | 8/2015 | Sugiura et al. |
| 2015/0248073 A1 | 9/2015 | Nakayama et al. |
| 2015/0248074 A1 | 9/2015 | Suzuki et al. |
| 2015/0253685 A1 | 9/2015 | Suzuki et al. |
| 2015/0253688 A1 | 9/2015 | Yamauchi et al. |
| 2016/0091812 A1 | 3/2016 | Makabe et al. |
| 2016/0223926 A1 | 8/2016 | Miyaake et al. |
| 2016/0327884 A1 | 11/2016 | Nakajima et al. |
| 2017/0139337 A1 | 5/2017 | Kaneko et al. |
| 2018/0067409 A1 | 3/2018 | Yamauchi et al. |
| 2018/0113391 A1 | 4/2018 | Yamauchi et al. |
| 2018/0259864 A1 | 9/2018 | Suzuki et al. |
| 2018/0267418 A1 | 9/2018 | Ogino et al. |

FOREIGN PATENT DOCUMENTS

| | | |
|---|---|---|
| JP | 2014-081468 | 5/2014 |
| JP | 2014-197144 | 10/2014 |
| JP | 2018-180239 | 11/2018 |
| WO | WO2018/190247 A1 | 10/2018 |

TONER, IMAGE FORMING APPARATUS, IMAGE FORMING METHOD, AND TONER ACCOMMODATING UNIT

CROSS-REFERENCE TO RELATED APPLICATIONS

This patent application is based on and claims priority pursuant to 35 U.S.C. § 119 to Japanese Patent Application Nos. 2017-247915 and 2018-205410, filed on Dec. 25, 2017 and Oct. 31, 2018, respectively, in the Japan Patent Office, the entire disclosures of which are hereby incorporated by reference herein.

BACKGROUND

Technical Field

The present disclosure relates to a toner, an image forming apparatus, an image forming method, and a toner accommodating unit.

Description of the Related Art

To form a full color image by electrophotography, a toner set of three process colors (also simply referred to as process color) of cyan toner, magenta toner, and yellow toner combined with black toner is used in general.

There is no limitation on the development order of toner to form a full color image. For example, a photoconductor is exposed to light from an original through a color separation filter or an image read by a scanner is written on a photoconductor with laser beams and exposed to light to form a latent electrostatic image of a yellow image portion on the photoconductor. This yellow toner image obtained by developing this latent electrostatic image with yellow toner is transferred to a recording medium, typically paper. Thereafter, a magenta toner image, a cyan toner image, and a black toner image obtained by using the magenta toner, the cyan toner, and the black toner in the same manner are sequentially overlapped on the yellow toner image, whereby a full color image is formed.

Also, as with a growing popularity of electrophotographic color image forming apparatuses, their usage has expanded in various ways, and the demand for enhancing image quality becomes strong. In particular, in the field of design, advertisement, etc., needs for colors not reproducible by the combination of typical process colors are increasing. In particular, in the field of security, the needs are increasing for invisible UV light emission toner, which is colorless and transparent under visible light but luminous under ultraviolet (UV) irradiation.

For such needs, an ultraviolet ray-excited ink composition using a europium complex having a specific structure has been proposed.

SUMMARY

According to the present invention, provided is an improved toner which includes a europium complex represented by the following Chemical formula 1,

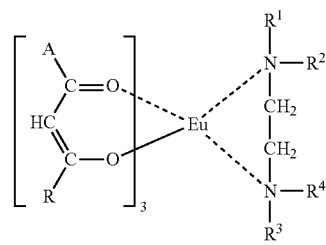

Chemical formula 1 where A represents 2-naphthyl group, 2-naphthyl group having a substitution group selected from the group consisting of an alkyl group, an alkoxy group, and a halogen, R represents a fluoroalkyl group having one to three carbon atoms or a methyl group, and $R^1$, $R^2$, $R^3$, and $R^4$ each, independently represent hydrogen atoms, alkyl groups, or aryl groups, wherein the toner has a hydroxyl value of from 20 to 40 mgKOH/g

BRIEF DESCRIPTION OF THE SEVERAL VIEWS OF THE DRAWINGS

A more complete appreciation of the embodiments and many of the attendant advantages and features thereof can be readily obtained and understood from the following detailed description with reference to the accompanying drawings, wherein.

Figure 1:
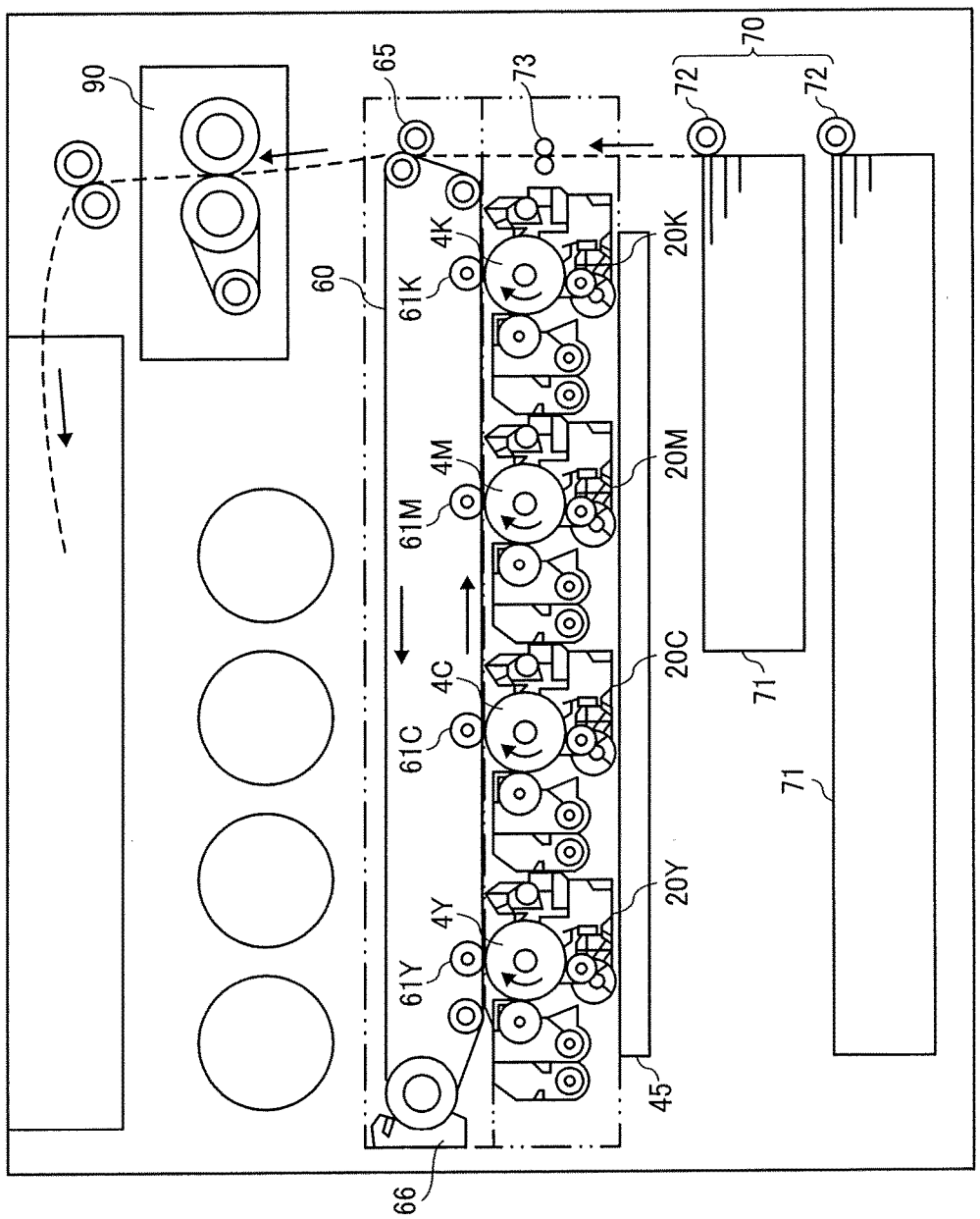
FIG. 1 is a schematic diagram illustrating an example of the image forming apparatus according to an embodiment of the present disclosure.

The accompanying drawings are intended to depict embodiments of the present invention and should not be interpreted to limit the scope thereof. The accompanying drawings are not to be considered as drawn to scale unless explicitly noted. Also, identical or similar reference numerals designate identical or similar components throughout the several views.

DESCRIPTION OF THE EMBODIMENTS

In describing embodiments illustrated in the drawings, specific terminology is employed for the sake of clarity. However, the disclosure of this specification is not intended to be limited to the specific terminology so selected and it is to be understood that each specific element includes all technical equivalents that have a similar function, operate in a similar manner, and achieve a similar result.

As used herein, the singular forms "a", "an", and "the" are intended to include the plural forms as well, unless the context clearly indicates otherwise.

Moreover, image forming, recording, printing, modeling, etc. in the present disclosure represent the same meaning, unless otherwise specified.

Having generally described preferred embodiments of this disclosure, further understanding can be obtained by reference to certain specific examples which are provided herein for the purpose of illustration only and are not intended to be limiting. In the descriptions in the following examples, the numbers represent weight ratios in parts, unless otherwise specified.

Toner

The toner of the present disclosure contains a europium complex represented by the following Chemical formula 1 and has a hydroxyl value of from 20 to 40 mgKOH/g.

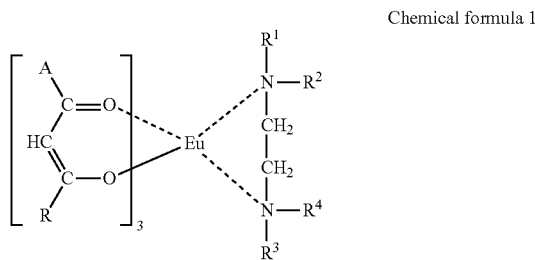

Chemical formula 1

In Chemical formula 1, A represents 2-naphthyl group, 2-naphthyl group having a substitution group selected from the group consisting of an alkyl group, an alkoxy group, and a halogen, R represents a fluoroalkyl group having one to three carbon atoms or a methyl group, and $R^1$, $R^2$, $R^3$, and $R^4$ each, independently represent hydrogen atoms, alkyl groups, or aryl groups.

Hereinafter, the toner of the present disclosure, a developer containing the toner, and the image forming apparatus of the present disclosure are described with reference to the accompanying drawings. It is to be noted that the following embodiments are not limiting the present disclosure and any deletion, addition, modification, change, etc. can be made within a scope in which man in the art can conceive including other embodiments, and any of which is included within the scope of the present disclosure as long as the effect and feature of the present disclosure are demonstrated.

The toner of the present disclosure is based on the knowledge that when the europium complex is used for toner, obtained chargeability is insufficient due to the material property. In addition, the toner of the present disclosure is based on the knowledge that there is no invisible UV light emission toner satisfying market demand and having a fluorescent coloring property sufficient for practical use yet.

The toner of the present disclosure contains the europium complex represented by Chemical formula 1 illustrated above, preferably contains a binder resin, a releasing agent, and further optionally other components.

The toner has a hydroxyl value of from 20 to 40 mgKOH/g.

Hydroxyl Value of Toner

The hydroxyl value of the toner is from 20 to 40 mgKOH/g and preferably from 30 to 40 mgKOH/g.

As a result of an investigation, the present inventors have found that the chargeability of toner containing a europium complex represented by Chemical formula 1 illustrated above greatly changes depending on the hydroxyl value of a binder resin. Within the range specified above, it was confirmed that the europium complex represented by Chemical formula 1 illustrated above was stably and sufficiently dispersed in the binder resin and desired chargeability could be obtained.

When the hydroxyl value of the toner is 20 mgKOH/g or greater, it is possible to prevent such a problem that the fluorescence intensity decreases as chargeability of the toner deteriorates. When the hydroxyl value of the toner is 40 mgKOH/g or less, it is possible to prevent such a problem that the toner agglomerates in a high temperature and high humidity conditions.

Since the hydroxyl value of the toner is almost equal to the hydroxyl value of the binder resin, which is the major component of the toner, the hydroxyl value of the toner can be adjusted by the hydroxyl value of the binder resin.

Measurement of Hydroxyl Value of Toner

The hydroxyl value of toner can be measured under the following conditions in accordance with the measuring method according to JIS K0070-1992 format.

1) Toner is dissolved in tetrahydrofuran (THF) and filtrated to remove the precipitate. The evaporated and solidified filtrate is used as a sample for measuring.
   0.5 to 2.0 g of the sample is precisely loaded in 200 mL flat bottom flask. The precisely loaded amount of the sample is determined as Wg.
2) 5 mL of acetylation reagent (all of 25 g of acetic acid anhydride is taken into a 100 mL flask and thereafter pyridine is added thereto to make the total 100 mL followed by thorough stirring) is added.
3) A small funnel is placed in an opening of the flask, whose lower part of about 1 cm from the bottom is bathed and heated in glycerin at 95 to 100 degrees C. To prevent the temperature rising of the neck of the flask caused by the heat of glycerin bathing, a thick paper disk having a round hole in the center is used to cap the neck of the flask.
4) One hour later, the flask is taken out of glycerin bath, subsequent to cooling, 1 mL of water is added to the flask through the funnel, which is thereafter shaken to decompose acetic anhydride.
5) Moreover, to completely dissolve acetic anhydride, the flask is heated again in glycerin bath for 10 minutes. Subsequent to cooling down, 5 mL of ethanol is used to rinse the funnel and the flask wall.
6) Several droplets of phenolphthalein solution are added as an indicator and 0.5 kmol/m$^3$ of potassium hydroxide ethanol solution is used for titration. The time when thin red color of the indicator lasts for about 30 seconds is determined as the terminal point.
7) A blank test is conducted for 2) to 6) without using a resin.
8) If the sample is not easily dissolved, a minute amount of pyridine is further added or xylene or toluene is added to dissolve the sample.

$A=[\{(B-C) \times 28.05 \times f\}/S]+D$

A: Hydroxyl value (mgKOH/g)
B: Amount (mL) of 0.5 kmol/m$^3$ potassium hydroxide ethanol solution for use in blank test
C: Amount (mL) of 0.5 kmol/m$^3$ potassium hydroxide ethanol solution for use in titration
f: factor of 0.5 kmol/m$^3$ potassium hydroxide ethanol solution
S: Amount of resin
D: Acid value
28.05: 56.11 (formula weight of potassium hydroxide)×½

Measurement of Acid Value of Toner

The acid value of the toner is measured under the following condition according to the measuring method described in JIS K0070-1992 format.

1) Toner is dissolved in tetrahydrofuran (THF) and filtrated to remove the precipitate. The evaporated and solidified filtrate is used as a sample for measuring.
   0.5 to 2.0 g of the sample is precisely loaded in 200 mL flat bottom flask. The precisely loaded amount of the sample is determined as Wg.

2) The sample is placed in a 300 mL beaker and 150 mL of a liquid mixture of toluene/ethanol (4/1) is added thereto to dissolve the sample.
3) 0.1 mol/L KOH ethanol solution and a potentiometric titration measuring device are used for measuring. For example, potentiometric titration measuring device (AT-400, winworkstation) and autoburette (ABP-410), both manufactured by KYOTO ELECTRONICS MANUFACTURING CO., LTD., are used for automatic titration.
4) The usage amount of KOH solution at this point is determined as S (mL). At the same time, blank is measured and the usage amount of KOH is determined as B (mL).
5) The acid value is calculated according to the following relation: f means the factor of KOH.

Acid value (mgKOH/g)={(S−B)×f×5.61}/W

Europium Complex

The europium complex is represented by the following chemical formula 1 and transparent under visible light and luminous under ultraviolet light irradiation.

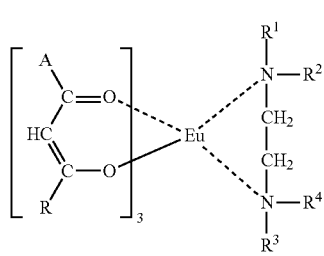

Chemical formula 1

In Chemical formula 1, A represents non-substituted 2-naphthyl group or 2-naphthyl group having a substitution group selected from the group consisting of an alkyl group, an alkoxy group, and a halogen, R represents a fluoroalkyl group having one to three carbon atoms or a methyl group, and $R^1$, $R^2$, $R^3$, and $R^4$ each, independently represent hydrogen atoms, alkyl groups, or aryl groups.

Specific examples of A include, but are not limited to, 2-naphthyl group, 2-naphthyl groups substituted with an alkyl group having 1 to 4 carbon atoms such as 1-methyl-2-naphthyl group, 3-methyl-2-naphthyl group, 4-methyl-2-naphthyl group, 5-methyl-2-naphthyl group, 6-methyl-2-naphthyl group, 7-methyl-2-naphthyl group, 8-methyl-2-naphthyl group, and 4-ethyl-2-naphthyl group, 2 naphthyl groups substituted with an alkoxy group having 1 to 4 carbon atoms such as 1-methoxy-2-naphthyl group, 3-methoxy-2-naphthyl group, 4-methoxy-2-naphthyl group, 5-methoxy-2-naphthyl group, 6-methoxy-2-naphthyl group, 7-methoxy-2-naphthyl group, 8-methoxy-2-naphthyl group, and 6-ethoxy-2-naphthyl group, and halogen-substituted 2-naphthyl group. Of these, 2-naphthyl group is preferable.

Specific examples of R include, but are not limited to, methyl group and fluoroalkyl groups having one to three carbon atoms such as $CF_3$ group, $CF_2H$ group, $CFH_2$ group, $C_3F_5$ group, $CH(CF_3)_2$ group, and $CF_2CF_2CF_3$ group. Of these, $CF_3$ group is preferable.

Specific examples of each of $R^1$, $R^2$, $R^3$, and $R^4$ include, but are not limited to, a hydrogen atom, an alkyl group having 1 to 5 carbon atoms such as a methyl group, an ethyl group, a propyl group, and a butyl group, and an aryl group such as a phenyl group and a substituted phenyl group. Of these, methyl group is preferable.

Of these europium complexes represented by Chemical formula 1 illustrated above, the europium complex represented by the following Chemical formula 2 is preferable.

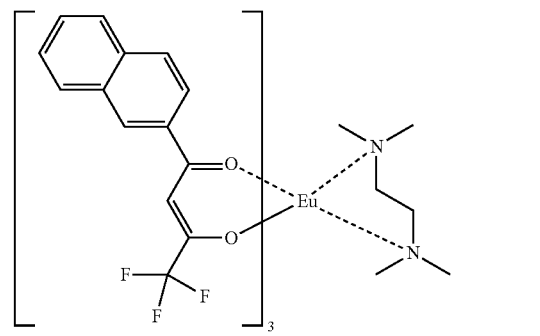

Chemical formula 2

The amount of the europium complex contained in the toner is preferably from 0.5 to 10.0 parts by mass based on 100 parts by mass of the total amount of the binder resin and the releasing agent in the toner or 100 parts by mass of just the binder resin in the toner when the releasing agent is not contained. When the amount of the europium complex in the toner is 0.5 parts by mass or greater, it is possible to prevent such problems that sufficient fluorescence intensity may not be obtained, so that the attached amount of toner to obtain a desired fluorescence intensity increases, the toner attached portion is noticeable even under visible light irradiation, and image quality deteriorates regarding granularity and fine-line reproducibility. When the amount is 10.0 parts by mass or less, it is possible to prevent such problems that charge-ability of the toner becomes unstable and the thermal properties of the toner is affected, which leads to degradation of fixability.

Properties of Toner

Glass Transition Temperature (Tg) of Toner and Half Efflux Temperature [T(F½)] of Toner The glass transition temperature (Tg) of the toner and the half efflux temperature [T(F½)] of the toner are preferably low unless both degrade high temperature and high humidity storage stability of the toner. For example, Tg is preferably from 45 to 75 degrees C. and more preferably from 50 to 60 degrees C. T(F½) is preferably from 90 to 150 degrees C. and more preferably from 105 to 120 degrees C.

When Tg and T(F½) are the upper limit specified above or lower and within the range specified above, it is possible to prevent such a problem that the toner fixing lower limit temperature becomes high, thereby degrading the toner lower temperature fixability. Moreover, it is also possible to prevent such a problem that gloss becomes too low, which increases the gloss difference between the toner and paper (recording medium) or other color toner attached image, thereby causing invisible UV emission toner attached image easily noticeable, meaning loss of invisibility.

When Tg and T(F½) are the lower limit or higher and within the range specified above, it is possible to prevent the problem that the high-temperature high-humidity storage stability and hot offset resistance deteriorate.

Measuring of Tg and T(F½)

A differential scanning calorimeter (DSC 210, manufactured by Seiko Instruments Inc.) is used for Tg measuring. 0.01 to 0.02 gram of a sample is weighted and loaded in an aluminum pan. The sample is heated to 200 degrees C., cooled down to 0 degrees C. at a temperature falling speed of 10 degrees C./minute, heated again at a temperature rising speed of 10 degrees C./minute. The intersection of the extended line of the base line equal to or lower than the endothermic maximum peak temperature and the tangent indicating the maximum gradient from the rising part of the peak to the peak apex is determined as Tg.

A flow tester (CFT-500D, manufactured by Shimadzu Corporation) is used for T(F½) measuring. While one gram of a sample is heated at a temperature rising speed of 6 degrees C./minute, the sample is under a load of 1.96 MPa by a plunger and extruded through a nozzle having a diameter of 1 mm and a length of 1 mm. The amount of lowering of the plunger of the flow tester is plotted against the temperature. The temperature at which a half of the sample is eluted off is determined as T(F½).

Molecular Weight of Toner Soluble Portion in Tetrahydrofuran (THF)

The weight average molecular weight (Mw) of the toner soluble portion in tetrahydrofuran (THF) is not particularly limited and can be suitably selected to suit to a particular application. Preferably, it is from 6,000 to 12,000 and more preferably from 7,000 to 10,000.

When the weight average molecular weight is not less than 6,000, it is possible to prevent such a problem that the glass transition temperature of the toner tends to be low, which leads to deterioration of storage stability of the toner, resulting in agglomeration of the toner in a storage environment. In addition, it can also prevent such a problem that viscoelasticity of the toner at high temperatures becomes excessively low, thereby impairing hot offset resistance of the toner. Moreover, it can prevent such a problem that the T(½) temperature lowers and the image gloss excessively increases, which invites an excessive gloss difference between the toner and the paper (recording medium) or other color toner attached image, which causes invisible UV emission toner attached image easily noticeable, meaning loss of invisibility.

When the weight average molecular weight is 12,000 or less, it is possible to prevent such a problem that viscoelasticity increases, ductility becomes inferior, thereby impairing low temperature fixability and gloss. Moreover, it can prevent such a problem that image gloss excessively decreases, which invites an excessive gloss difference between the toner and the paper (recording medium) or other color toner attached image, thereby causing invisible UV emission toner attached image easily noticeable, meaning loss of invisibility.

The weight average molecular weight of the toner can be obtained by measuring the molecular weight distribution of the toner soluble portion in tetrahydrofuran (THF) by a gel permeation chromatography (GPC) measuring instrument (GPC-150C, manufactured by Waters Corporation).

A column (KF801 to 807, manufactured by SHOWADENKO K.K) is used in the measuring and the following method is utilized: The column is stabilized in a heat chamber at 40 degrees C. and THF is caused to flow as solvent at 1 mL/min in the column at this temperature. Thereafter, 0.05 g of a sample and 5 g of THF are mixed and stirred at 22 to 24 degrees C. for 24 hours followed by filtration by a filter for pre-processing (for example, Chromatodisc having an average pore diameter of 0.45 μm, manufactured by Kurabo Industries Ltd.). Thereafter, the filtrate is adjusted in such a manner that the sample concentration is from 0.05 to 0.6 percent by mass and 50 to 200 μL of the THF sample solution of the resin is infused into the column for measuring.

With regard to measuring of the weight average molecular weight Mw and the number average molecular weight Mn of the THF solution of the sample, the molecular weight distribution of the sample is calculated by the relation between the logarithm values of the standard curves created from several kinds of the mono-dispersed polystyrene standard samples and the count figures.

As the standard polystyrene sample for the standard curve, it is suitable to use at least about ten standard polystyrene samples among, for example, polystyrene samples having a molecular weight of $6\times10^2$, $2.1\times10^2$, $4\times10^2$, $1.75\times10^4$, $5.1\times10^4$, $1.1\times10^5$, $3.9\times10^5$, $8.6\times10^5$, $2\times10^6$, or $4.48\times10^6$, manufactured by TOSOH CORPORATION or Pressure Chemical Co. A refractive index (RI) detector is used as the detector.

Each Component Analysis of Toner

Analysis of Fluorescent Colorant by Component Analysis according to Gas Chromatography Mass Spectroscopy (GC-MS)

The fluorescent colorant in the toner can be confirmed and quantified according to the following procedures, devices, and conditions.

Sample Processing

Approximately 1 μL of a methylating agent [20 percent methanol solution of tetramethylammonium hydroxide (TMAH)] is dripped on about 1 mg of a sample to obtain a sample.

Measuring

Pyrolysis-gas chromatograph mass spectrometry (Py-GCMS) meter

Analyzer: QP2010, manufactured by Shimadzu Corporation

Heating furnace: Py2020 D, manufactured by Frontier Laboratories Ltd.

Heating Temperature: 320 degrees C.

Column: Ultra ALLOY-5L=30 m I.D=0.25 mm

Film=0.25 μm

Column temperature: 50 degrees C. (held for 1 minute)–heated (10 degrees C./minute) to 340 degrees C. (held for 7 minutes)

Split ratio: 1:100

Column flow rate: 1.0 mL/min

Ionization method: EI method (70 eV)

Measuring mode: Scan mode

Data for retrieval: NIST 20 MASS SPECTRAL LIB.

Analysis of Fluorescent Colorant by Component Analysis According to NMR

The fluorescent colorant in the toner can be confirmed and quantified according to the following procedures, devices, and conditions.

Sample Preparation (1) For $^1$H-NMR

About 40 to 50 mg of a sample is dissolved in about 0.7 mL (d=1.48) of CDCl$_3$ containing TMS.

(2) For $^{13}$C-NMR

About 250 to 260 mg of a sample is dissolved in about 0.7 mL (d=1.48) of CDCl$_3$ containing TMS.

Analyzer/Measuring Condition

ECX-500 NMR instrument, manufactured by JEOL Ltd.

(1) Measurement nucleus=$^1$H (500 MHz), measuring pulse file=single pulse ex 2 (1H), 45 degree pulse Integration 16 times, Relaxation Delay 5 seconds, Data point 32K, Observation width=15 ppm (2) Measurement nucleus=$^{13}$C (125 MHz), measuring pulse file=single pulse dec. ex 2 (1H), 30 degree pulse Integration 1,000 times (1039 times only for RNC-501), Relaxation Delay 2 seconds, data point 32K Offset 100 ppm, Observation width=250 ppm Binder Resin In the present disclosure, the binder resin (resin for fixing) used as a toner material is not particularly limited and can be suitably selected to suit to a particular application. Typical resins can be used.

Specific examples of the binder resin include, but are not limited to, styrene, styrene-based resins (homopolymers or copolymers of styrene or styrene substitute) such as poly-α-styrene, styrene-chlorostyrene copolymers, styrene-propylene copolymers, styrene-butadiene copolymers, styrene-vinyl chloride copolymers, styrene-vinyl acetate copolymer, styrene-maleic acid copolymer, styrene-acrylic acid ester copolymer, styrene-methacrylic acid ester copolymer, styrene-α-chloroacrylic acid methyl copolymer, and styrene-acrylonitrile-acrylic acid-ester copolymers, epoxy resins, vinyl chloride resins, rosin-modified maleic acid resins, phenol resins, polyethylene resins, polypropylene resins, petroleum resins, polyurethane resins, ketone resins, ethylene-ethyl acrylate copolymers, xylene resins, and polyvinyl butyrate resins. In addition, the method of manufacturing these resins is also not particularly limited. Any of bulk polymerization, solution polymerization, emulsion polymerization, and suspension polymerization can be utilized.

In the present disclosure, it is preferable to contain a polyester resin as the binder resin (resin for fixing) and more preferably a polyester resin as the major component. Polyester resins can generally be fixed at low temperatures while keeping high temperature and high humidity storage stability in comparison with other resins. Therefore, polyester resins are suitable as the binder resin for the present disclosure.

Polyester resins for use in the present disclosure are obtained by polycondensation of an alcohol and a carboxylic acid.

Specific examples of the alcohol include, but are not limited to, glycols such as ethylene glycol, diethylene glycol, triethylene glycol, and propylene glycol, 1,4-bis(hydroxymethyl)cyclohexane, etherified bisphenols such as bisphenol A, diol monomers, tri- or higher polyol monomers.

Specific examples of the carboxylic acid include, but are not limited to, di-valent organic acid monomers such as maleic acid, fumaric acid, phthalic acid, isophthalic acid, terephthalic acid, succinic acid, and malonic acid; and tri- or higher carboxylic acid monomers such as 1,2,4-benzene tricarboxylic acid, 1,2,5-benzene tricarboxylic acid, 1,2,4-cyclohexane tricarboxylic acid, 1,2,4-naphthalene tricarboxylic acid, 1,2,5-hexane tricarboxylic acid, 1,3-dicarboxyl-2-methylene carboxy propane, and 1,2,7,8-octane tetracarboxylic acid.

Tg of the polyester resin is preferably from 50 to 75 degrees C.

Releasing Agent

The releasing agent is not particularly limited and can be suitably selected to suit to a particular application. The releasing agent can be used alone or in combination.

To overlap an image on a toner layer, the toner layer (fluorescent toner layer) existing on the outermost surface is required to have particularly high hot offset resistance. Inclusion of a releasing agent in the toner can increase the releasing property with a fixing member.

The releasing agent is not particularly limited and can be suitably selected to suit to a particular application.

Specific examples include, but are not limited to, aliphatic hydrocarbons such as liquid paraffin, microcrystalline wax, natural paraffin, synthetic paraffin, polyolefin wax, and partial oxides, fluorides, and chlorides thereof; animal oil such as beef tallow and fish oil; vegetable oils such as coconut oil, soybean oil, rapeseed oil, rice bran wax, and carnauba wax; higher aliphatic alcohol or aliphatic acid such as montan wax; aliphatic acid amide, aliphatic acid bisamide; metal soap such as zinc stearate, calcium stearate, magnesium stearate, aluminum stearate, zinc oleate, zinc palmitate, magnesium palmitate, zinc myristate, zinc laurate, and zinc behenate; aliphatic acid esters, and polyvinylidene fluoride.

Other Components

The toner of the present disclosure may contain other components such as a charge control agent and an inorganic particulate (external additive) for external addition.

Charge Control Agent

The toner may contain a charge control agent.

The charge control agent is not particularly limited and can be suitably selected to suit to a particular application.

Specific examples include, but are not limited to, modified products such as nigrosine and metal salts of aliphatic acids; onium salts such as phosphonium salts and lake pigments thereof; triphenylmethane dyes and lake pigments thereof; metal salts of higher aliphatic acids; diorganotin oxides such as dibutyltin oxide, dioctyltin oxide and dicyclohexyltin oxide; diorganotin borates such as dibutyltin borate, dioctyltin borate, dicyclohexyltin borate; organometallic complexes, chelate compounds, monoazo metal complexes, acetylacetone metal complexes, metal complexes of aromatic hydroxycarboxylic acids and aromatic dicarboxylic acid; quaternary ammonium salts; aromatic hydroxycarboxylic acid, aromatic mono- and polycarboxylic acid and metal salts thereof, anhydrides, esters; and phenol derivatives such as bisphenol.

These can be used alone or in combination.

When the charge control agent is added to the inside of the toner, it is preferably 0.1 to 10 parts by mass based on 100 parts by mass of the binder resin. In addition, the charge control agent may affect the color of toner. Therefore, it is preferable to select a transparent charge control agent as much as possible except for black toner.

Inorganic Particulate For External Addition

The inorganic particulates (external additive) for external addition for use in the present disclosure is not particularly limited and can be suitably selected to suit to a particular application.

Specific examples include, but are not limited to, silica, alumina, titanium oxide, barium titanate, magnesium titanate, calcium titanate, strontium titanate, zinc oxide, silica sand, clay, mica, wollastonite, diatomaceous earth, chromium oxide, cerium oxide, iron oxide, antimony trioxide, magnesium oxide, zirconium oxide, barium sulfate, barium carbonate, calcium carbonate, silicon carbide, and silicon nitride. Of these, silica, alumina, and titanium oxide are preferable.

In addition, as the inorganic particulate, articles surface-treated with a hydrophobizing agent may be used.

Specific examples of the hydrophobizing agent include, but are not limited to, silane coupling agents, silylation agents, silane coupling agents including a fluoroalkyl group, organic titanate coupling agents, and aluminum coupling agents.

Also, silicone oil can be used as a hydrophobizing agent.

The inorganic particulate preferably has an average primary particle diameter of from 5 to 500 μm and more preferably from 5 to 200 nm. When the thickness is 5 nm or greater, it is possible to prevent such a problem that aggregation of the inorganic particulates occurs, which leads to non-uniform dispersion of the inorganic particulates in the toner. When the thickness is 500 nm or less, improvement on high temperature and high humidity storage stability can be expected due to filler effects.

The average primary particle diameter can be directly measured from a photograph obtained by a transmission electron microscope. It is preferable to observe at least 100 particles and use the average value of major diameters thereof.

Method of Manufacturing Toner

Known methods can be appropriately used as the method of manufacturing the toner as long as it can satisfy the above-mentioned requirements defined in the present disclosure.

Specific examples include, but are not limited to, a kneading pulverization method and a so-called chemical method such as granulation of toner particles in an aqueous medium.

For example, in order to prepare the toner of the present disclosure, firstly, the europium complex, the binder resin, optional releasing agents and inorganic particulates, and further optional charge control agents are combined and thoroughly mixed by a mixer such as a Henschel mixer or a super mixer. Thereafter, heat-melting mixing kneaders such as a heating roller, a kneader, and an extruder are used to thoroughly melt-knead the raw materials. Subsequent to cooling and solidification, the mixture is finely-pulverized and classified to obtain toner. As the pulverization method, it is possible to employ a jet mill method of adding toner to a jet air followed by collision with a collision board to pulverize the toner utilizing its collision energy, an inter-particle collision method of colliding toner particles in an air stream, or a mechanical pulverization method of supplying toner into a narrow gap with a rotor rotating at high speed.

In addition, to manufacture the toner of the present disclosure, a dissolution suspension method can be employed in which an oil phase in which toner materials are dissolved or dispersed in an organic solvent phase is dispersed in an aqueous medium phase to allow resin reaction followed by removal of the solvent, filtration and rinsing, and drying to manufacture mother toner particles.

Developer

The developer of the present disclosure contains at least the toner mentioned above. The developer may be a one-component developer or a two-component developer.

In a preferred embodiment, the toner of the present disclosure is mixed with magnetic carrier to form a two-component developer, which is used in an electrophotographic image forming method using a two-component developer.

When employing the two-component development method, spinel ferrites such as magnetite and gamma ferric oxide, spinel ferrites having one or two kinds of metals Mn, Ni, Zn, Mg, Cu, etc other than iron, magnetoplumbite type ferrites such as barium ferrite, and iron or alloyed metal particles having an oxidized layer on the surface can be used as magnetic particulates for use in the magnetic carrier.

These particulates can take spherical form, needle-like form, etc. In particular, for strong magnetization, it is preferable to use ferromagnetic particulates such as iron. In addition, in terms of chemical stability, it is preferable to use spinel ferrite such as magnetite and gamma ferric oxide and magnetoplumbite type ferrite such as barium ferrite.

Specifically, MFL-355, MFL-35HS (both manufactured by Powdertech CO., Ltd.), DFC-400M, DFC-410M, and SM-350NV (all manufactured by DOWA IP Creation Co., Ltd.) are suitable.

It is possible to use resin carrier having a desired magnetization obtained by selecting a combination and the amount of ferromagnetic particulates. Such carrier has a magnetization of from 30 to 150 emu/g in 1,000 oersted. Such resin carriers can be manufactured by spraying a melt-kneaded material of magnetized particulates and a binder resin having insulation property by a spray drier. Also, it is possible to manufacture resin carrier in which magnetized particulates are dispersed in a condensation type binder formed by reacting and curing monomers or prepolymers in an aqueous medium under the presence of magnetized particulates.

To control the chargeability of magnetized carrier, positively or negatively charged particulates or electroconductive particulates are fixated on the surface of the magnetized carrier or the surface is coated with a resin.

As the coating material (resin) for the surface of magnetized carrier, silicone resins, acrylic resins, epoxy resins, fluorochemical resins, etc. are used. Furthermore, the surface thereof can be coated with a material containing positively or negatively charged particulates or electroconductive particulates. Of these, silicone resins and acrylic resins are preferable.

In the present disclosure, the mass ratio of the carrier in the developer accommodated in a developing device is preferably 85 to less than 98 percent by mass. When it is 85 percent by mass or more, it is possible to reduce occurrence of a defective image caused by frequent scattering of toner from the developing device. When the mass ratio of the carrier in the developer is less than 98 percent by mass, it is possible to prevent the charge amount of the electrophotographic development toner from excessively increasing and the supply amount of the electrophotographic development toner from excessively decreasing, thereby effectively preventing an image density decrease and production of defective images.

Image Forming Apparatus and Image Formation Method

The image forming apparatus of the present disclosure includes a latent electrostatic image bearer, a latent electrostatic image forming device, a developing device, and other optional devices.

The image forming method of the present disclosure includes a latent electrostatic image forming process, a developing process, and other optional processes.

The image forming method can be suitably conducted by the image forming apparatus. The latent electrostatic image forming process can be suitably conducted by the latent electrostatic image forming device. The developing process can be suitably conducted by the developing device. The other optional processes can be suitably conducted by the corresponding other optional devices.

The image forming apparatus more preferably includes a latent electrostatic image bearer, a latent electrostatic image forming device to form a latent electrostatic image on the latent electrostatic image bearer, a developing device to develop the latent electrostatic image on the latent electrostatic image bearer with toner to form a toner image, a transfer device to transfer the toner image onto the surface of a recording medium, and a fixing device to fix the toner image on the surface of the recording medium.

The image forming method more preferably includes forming a latent electrostatic image on a latent electrostatic image bearer, developing the latent electrostatic image formed on the latent electrostatic image bearer with toner to form a toner image, transferring the toner image formed on the latent electrostatic image bearer to the surface of a recording medium, and fixing the toner image transferred to the surface of the recording medium.

The toner mentioned above is used in the developing device and the developing process. It is preferable to form the toner image using a developer containing the toner and optional other components such as carrier.

The image forming apparatus of the present disclosure includes the developing device containing a combination of multiple color toners. The multiple color toners include the toner (invisible UV light emission toner) of the present disclosure and other color toners appropriately selected to suit to an application purpose.

For example, the image forming apparatus preferably includes five developing devices for black, cyan, magenta, yellow, and the toner of the present disclosure.

As the other color toners for use in the combination with the toner (for example, fluorescent pink color toner) of the present disclosure, examples are the following colorant-containing toners.

For example, process color toners of black, cyan, magenta, and yellow, and special color toners such as white toner, green toner, blue toner, and metallic toner are included.

The colorant used for these toners is not particularly limited. It is possible to appropriately select and use a commonly-used colorant.

Using simple carbon black or a mixture of carbon black with a copper phthalocyanine, etc. is preferable to adjust hue and luminosity as the black toner.

As the cyan toner, copper phthalocyanine, which is Pigment Blue 15:3, or a mixture obtained by mixing aluminum phthalocyanine with the colorant is preferable.

Pigment Red 53:1, Pigment Red 81, Pigment Red 122, and Pigment Red 269 are used alone or in a combination as the magenta toner.

Pigment Yellow 74, Pigment Yellow 155, Pigment Yellow 180 and Pigment Yellow 185 are used alone or in a combination as the yellow toner. It is preferable to use simple Pigment Yellow 185 or a mixture thereof with Pigment Yellow 74 in terms of color and storage stability.

As the white toner, titanium dioxide surface-treated with silicon, zirconia, aluminum, and polyol can be used.

As the green toner, Pigment Green 7, etc. can be used. However, it is necessary to pay attention to safety.

Specific examples of the blue toner include, but are not limited to, Pigment Blue 15:1 and Pigment Violet 23.

Figure 3:
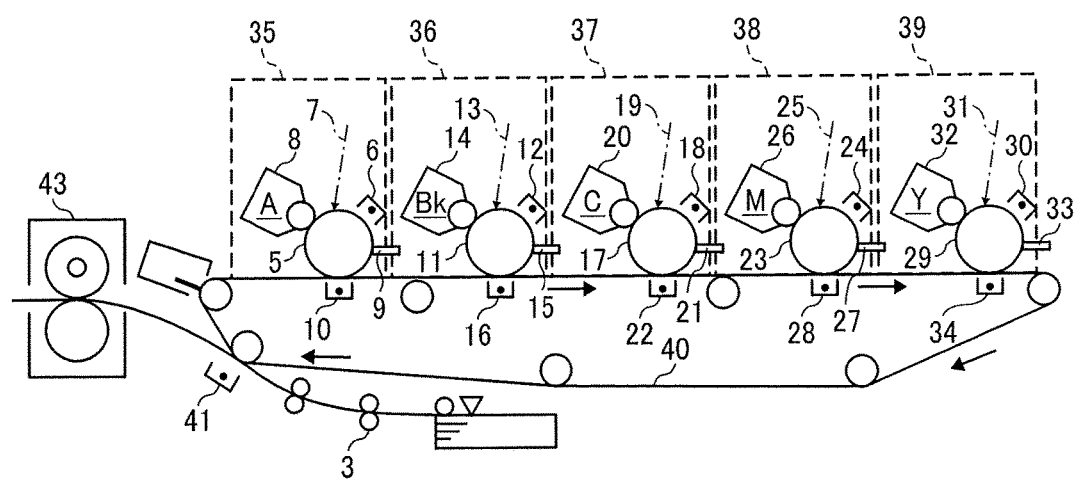
FIG. 3 is a schematic diagram illustrating another example of the image forming part of the image forming apparatus according to an embodiment of the present disclosure.

FIG. 1 is a schematic diagram illustrating an image forming apparatus according to an embodiment of the present disclosure. In FIG. 1, the developing device for the toner of the present disclosure is omitted. However, the image forming apparatus includes the developing device for the toner of the present disclosure in the same manner as the developing devices for the toners of yellow, cyan, magenta, and black (FIG. 3). The image forming apparatus illustrated in FIG. 1 employs a so-called tandem type intermediate transfer belt method (multiple image bearer method), which includes toner image forming units 20Y, 20C, 20M, 20K, and 20A disposed side by side for yellow, cyan, magenta, black, and the toner of the present disclosure, respectively, and overlaps the color toner images of yellow (Y), cyan (C), magenta (M), black (B), and the toner (A) of the present disclosure formed by the toner image forming units to form a full color image. The arrangement order of the toner image forming units is not particularly limited.

Individual toner image forming units 20Y, 20C, 20M, 20K, and 20A respectively include drum photoconductors 4Y, 4C, 4M, 4K, and 4A rotationally driven as the image bearers. In addition, an exposure device 45 is disposed to irradiate each of the drum photoconductors 4Y, 4C, 4M, 4K, and 4A with laser beams or LED light based on image information of each color to form latent images.

An intermediate transfer belt 60 as an intermediate transfer member is disposed so as to be surface-movable facing each of the toner image forming units 20Y, 20C, 20M, 20K, and 20A. Primary transfer rollers 61Y, 61C, 61M, 61K, and 61A to transfer the toner images of the respective colors formed on the drum photoconductors 4Y, 4C, 4M, 4K, and 4A to the intermediate transfer belt 60 are respectively disposed at positions facing the drum photoconductors 4Y, 4C, 4M, 4K, and 4A via the intermediate transfer belt 60.

The primary transfer rollers 61Y, 61C, 61M, 61K, and 61A sequentially transfer the color toner images formed by the toner image forming units 20Y, 20C, 20M, 20K, and 20A, which is described later, onto the intermediate transfer belt 60 to form a full-color image thereon.

A secondary transfer device 65 that collectively transfers the toner image on the intermediate transfer belt 60 onto a transfer sheet is disposed downstream of the primary transfer rollers 61Y, 61C, 61M, 61K, and 61A in the surface moving direction of the intermediate transfer belt 60. Further, a belt cleaning device 66 to remove toner remaining on the surface of the intermediate transfer belt 60 is disposed downstream of the secondary transfer device 65.

A sheet feeding unit 70 including sheet feeding cassettes 71, sheet feeding rollers 72, etc. is disposed at the bottom of the image forming apparatus and feeds the transfer sheet toward registration rollers 73. The registration rollers 73 send the transfer sheet toward the opposing portion of the intermediate transfer belt 60 and the secondary transfer device 65 in accordance with the timing of the toner image formation. The full color toner image on the intermediate transfer belt 60 is transferred onto the transfer sheet by the secondary transfer device 65, fixed by the fixing device 90, and thereafter ejected outside the machine.

Figure 2:
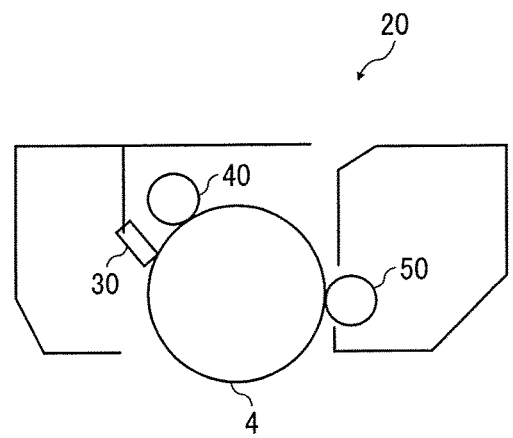
FIG. 2 is a schematic diagram illustrating an example of the image forming part of the image forming apparatus according to an embodiment of the present disclosure.

Next, each of the toner image forming units 20Y, 20C, 20M, 20K, and 20A is described. Since the configuration and operation of each of the toner image forming units 20Y, 20C, 20M, 20K, and 20A are substantially the same except that the color of the accommodated toner is different, the suffixes Y, C, M, K, and A are omitted in the following description of the configuration and operation of the toner image forming unit 20. FIG. 2 is a schematic diagram illustrating the configuration of a toner image forming part according to an embodiment of the image forming apparatus.

Various devices for conducting the electrophotographic process such as a charging device 40, a developing device 50, a cleaning device 30, etc. are disposed around the drum photoconductor 4 of the toner image forming units 20 to form each color toner image on the drum photoconductor 4 by known operations. Such a toner image forming unit 20 can be a process cartridge integrated in and detachable from the image forming apparatus.

FIG. 3 is a schematic diagram illustrating an example of the configuration of an image forming apparatus including five developing devices. The overlapping description of the image forming apparatus described above is omitted.

The image forming apparatus of the present embodiment includes photoconductors 5, 11, 17, 23, and 29. Around the photoconductors, chargers 6, 12, 18, 24, and 30, developing devices 8, 14, 20, 26, and 32, transfer devices 10, 16, 22, 28, and 34, and cleaning devices 9, 15, 21, 27, and 33 are disposed. The photoconductors 5, 11, 17, 23, and 29 are respectively irradiated with exposure light 7, 13, 19, 25, and 31.

Each color developing unit includes the photoconductor, the charger, the developing device, the cleaning device, etc. The developing unit 35 forms an image with the toner of the present disclosure, the developing unit 36 forms an image with a black toner, the developing unit 37 forms an image with a cyan toner, the developing unit 38 forms an image with a magenta toner, and the developing unit 39 forms an image with a yellow toner. Each developing unit transfers the image to the intermediate transfer belt 40 to form an image. The image formed on the intermediate transfer belt 40 is transferred onto a recording medium by a transfer device 41 and fixed by a fixing device 43.

In the present disclosure, the transfer material is also referred to as a recording medium, a recording material, a transfer sheet (paper), a recording paper, etc. There is no particular limit thereto and a known material can be used.

Figure 4:
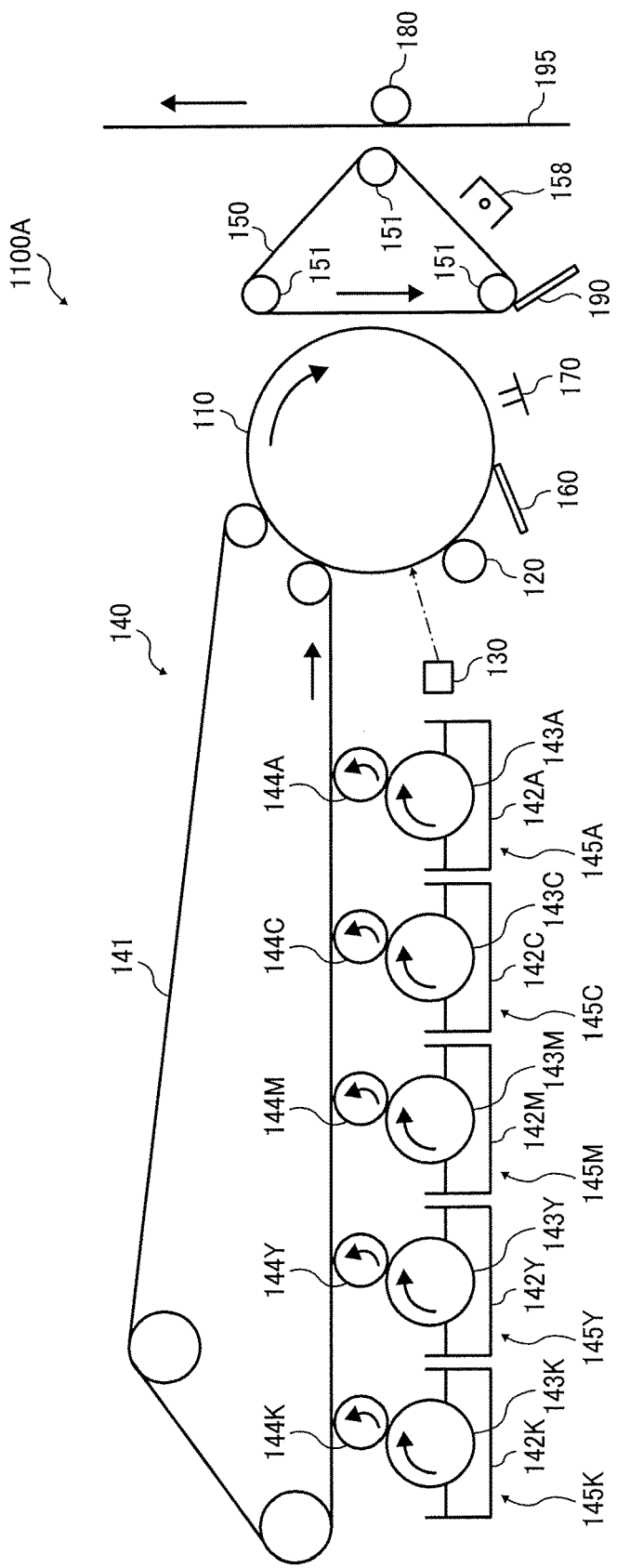
FIG. 4 is a schematic diagram illustrating another example of the image forming apparatus according to an embodiment of the present disclosure.

FIG. 4 is a schematic diagram illustrating another example of the image forming apparatus according to an embodiment of the present disclosure.

A color image forming apparatus 1100 A illustrated in FIG. 4 employs a revolver intermediate transfer belt method (single photoconductor method) and includes a drum photoconductor 110 (hereinafter, also referred to as photoconductor 110 as the latent electrostatic image bearer, a charging roller 120 as the charging device, an irradiator 130 as the exposing device, a developing unit 140 as the developing device, an intermediate transfer body 150, a cleaner 160 as the cleaning device having a cleaning blade, and a discharging lamp 170 as the discharging device.

The intermediate transfer body 150 is a belt having an endless form and is designed to be movable in the direction indicated by the arrow by three rollers 151 which are disposed inside the intermediate transfer body 150 and stretches the intermediate transfer body 150.

The three rollers 151 partially serves as a transfer bias roller to apply a transfer bias (primary transfer bias) to the intermediate transfer body 150.

Around the intermediate transfer body 150 is disposed a cleaner 190 including a cleaning blade.

Around the intermediate transfer body 150, a transfer roller 180 is disposed as the transfer device capable of applying a transfer bias to transfer (secondary transfer) a developed image (toner image) onto a transfer paper 195 as a recording medium while facing the intermediate transfer body 150.

Around the intermediate transfer body 150, a corona charger 158 to apply charges to the toner image on the intermediate transfer body 150 is disposed between the contact portion of the drum photoconductor 110 and the intermediate transfer body 150 and the contact portion between the intermediate transfer body 150 and the transfer sheet 195 along the rotation direction of the intermediate transfer body 150.

The developing device 140 includes a developing belt 141 as the developer bearer, a black (Bk) developing unit 145K, a yellow (Y) developing unit 145Y, a magenta (M) developing unit 145M, a cyan (C) developing unit 145C, and a developing unit 145A containing the toner of the present disclosure, all of which are disposed around the developing belt 141.

The black developing unit 145K includes a developer accommodating unit 142K, a developer supplying roller 143K, and a developing roller 144K.

The yellow developing unit 145Y includes a developer accommodating unit 142Y, a developer supplying roller 143Y, and a developing roller 144Y.

The magenta developing unit 145M includes a developer accommodating unit 142M, a developer supplying roller 143M, and a developing roller 144M.

The cyan developing unit 145C includes a developer accommodating unit 142C, a developer supplying roller 143C, and a developing roller 144C.

The unit 145A includes a developer accommodating portion 142A, a developer supply roller 143A, and a developing roller 144A.

Further, the developing belt 141 is a belt having an endless form, stretched around a plurality of belt rollers in a rotatable manner, and partially contacts with the photoconductor 110.

Specific aspects of the image forming method will be described below.

The image processing unit (hereinafter referred to as IPU) to which image data are sent creates each image signal of five kinds (five colors) of Y (yellow), M (magenta), C (cyan), K (black), Next, each image signal of Y, M, C, K and A is transmitted to the writing unit in the image processing unit.

The writing unit modulates and scans the five laser beams for Y, M, C, K, and A, and the charging unit charges the drum photoconductor to sequentially form latent electrostatic images on the drum photoconductors.

For example, the first drum photoconductor, the second drum photoconductor, the third drum photoconductor, the fourth drum photoconductor, and the fifth drum photoconductor respectively correspond to K, Y, M, C, and A.

Next, the developing unit as the developing device forms various (each color) toner images on the drum photoconductor.

In addition, the transfer sheet fed by the sheet feeding unit is conveyed on a transfer belt. The toner images on the drum photoconductors are sequentially transferred to the transfer sheet by transfer chargers.

After completion of this transfer step, the transfer sheet is conveyed to a fixing unit, where the transferred toner image is fixed on the transfer sheet. Also, after the completion of the transfer step, the toner remaining on the drum photoconductor is removed by the cleaning device.

Toner Accommodating Unit

The toner accommodating unit in the present disclosure contains toner in a unit capable of accommodating the toner. Examples of the toner accommodating unit are a toner accommodating container, a developing device, and a process cartridge.

The toner accommodating container is a vessel containing toner.

The developing device accommodates toner and develops an image with toner.

The process cartridge integrally includes at least a latent electrostatic image bearer (also referred to as an image bearer) and a developing device, accommodates toner, and is detachably attachable to an image forming apparatus. The process cartridge may further include at least one member selected from a charger, an exposure, and a cleaning device.

When the toner accommodating unit of the present disclosure is mounted onto an image forming apparatus and images are formed, it is possible to form images with the toner (invisible UV light emission toner) having fluorescent light emission properties under ultraviolet irradiation, which cannot be reproduced by a typical process color.

EXAMPLES

Next, the present disclosure is described in detail with reference to Examples but is not limited thereto. "Part"

Manufacturing Example of Toner 1

Polyester resin RN-290 (hydroxyl value of 35.8 mgKOH/g, manufactured by Kao Corporation): 15.8 parts
Polyester resin RN-306 (hydroxyl value of 39.5 mgKOH/g, manufactured by Kao Corporation): 78.9 parts
Carnauba wax WA-05 (manufactured by Cerarica NODA Co., Ltd.): 5.3 parts
Europium complex represented by the following Chemical formula 2: 4.0 parts Chemical formula 2

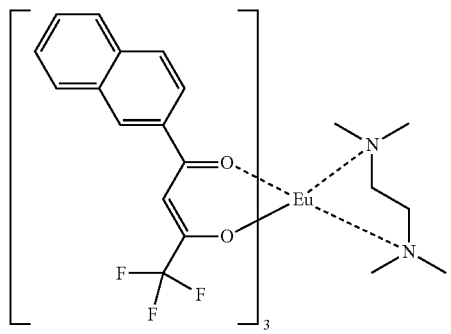

In the present disclosure, the europium complex represented by Chemical formula 2 illustrated above was obtained by the method disclosed in JP-2002-173622-A.

The toner materials specified above were preliminarily mixed by a HENSCHEL MIXER (FM20B, manufactured by NIPPON COKE & ENGINEERING CO., LTD.) and thereafter, melt-kneaded at 100 to 130 degrees C. by a one-shaft kneader (Ko-Kneader, available from BUSS AG). The thus-obtained kneaded mixture was cooled down to room temperature and coarsely pulverized to 200 to 300 μm by a pulverizer (Rotoplex). Next, using a counter jet mill (100 AFG, manufactured by Hosokawa Micron Corporation), the coarsely-pulverized resultant was finely-pulverized to have a weight average particle diameter of from 5.9 to 6.5 μm while appropriately adjusting the pulverization air pressure. Thereafter, in an air classifier (EJ-LABO, manufactured by Matsubo Corporation), the finely-pulverized resultant was classified to obtain mother toner particles having a weight average particle diameter of from 6.8 to 7.2 μm and a ratio of the weight average particle diameter to the number average particle diameter of 1.20 or lower while appropriately adjusting the louver opening.

Thereafter, 1.0 part of an additive (HDK-2000, manufactured by Clariant (Japan) K. K.) and 1.0 part of an additive (H05TD, manufactured by Clariant (Japan) K. K.) were stirred and mixed with 100 parts of the mother toner particles to manufacture Toner 1.

The toner particle (Toner 1) prepared as described above had a hydroxyl value of 38.9 mgKOH/g, a weight average molecular weight (Mw) of 11,461, a Tg of 56.9 degrees C., and a T(½) of 107.6 degrees C.

The hydroxyl value of the toner was measured in accordance with the measuring method according to JIS K0070-1992 format. The molecular weight distribution of the THF soluble portion was measured with a gel permeation chromatography (GPC) measuring device GPC-150C (manufactured by Nihon Waters K. K.) and Mw was calculated based on the calibration curve prepared from several types of mono-dispersion polystyrene standard samples. Tg was measured using a differential scanning calorimeter (DSC 210, manufactured by Seiko Instruments Inc.). T(½) was measured using a flow tester (CFT-500D, manufactured by Shimadzu Corporation).

Manufacturing Example of Toner 2

Polyester resin RN-290 (hydroxyl value of 35.8 mgKOH/g, manufactured by Kao Corporation): 15.8 parts
Polyester resin RN-263 (hydroxyl value of 49.0 mgKOH/g, manufactured by Kao Corporation): 78.9 parts
Carnauba wax WA-05 (manufactured by Cerarica NODA Co., Ltd.): 5.3 parts
Europium complex represented by the following Chemical formula 2: 4.0 parts
Toner 2 was manufactured in the same manner as Toner 1 except that the toner raw materials were changed as specified above.

The toner particles (Toner 2) prepared as described above had a hydroxyl value of 46.8 mgKOH/g, an Mw of 7.251, a Tg of 57.4 degrees C., and a T(½) of 106.2 degrees C.

Manufacturing Example of Toner 3

Polyester resin RN-290 (hydroxyl value of 35.8 mgKOH/g, manufactured by Kao Corporation): 15.8 parts
Polyester resin RN-300 (hydroxyl value of 31.0 mgKOH/g, manufactured by Kao Corporation): 78.9 parts
Carnauba wax WA-05 (manufactured by Cerarica NODA Co., Ltd.): 5.3 parts
Europium complex represented by Chemical formula 2 illustrated above: 4.0 parts
Toner 3 was manufactured in the same manner as Toner 1 except that the toner raw materials were changed as specified above.

The toner particle (Toner 3) prepared as described above had a hydroxyl value of 31.8 mgKOH/g, an Mw of 8.301, a Tg of 57.0 degrees C., and a T(½) of 114.6 degrees C.

Manufacturing Example of Toner 4

Polyester resin RN-290 (hydroxyl value of 35.8 mgKOH/g, manufactured by Kao Corporation): 15.8 parts
Polyester resin RLC-16 (hydroxyl value of 16.5 mgKOH/g, manufactured by Kao Corporation): 78.9 parts
Carnauba wax WA-05 (manufactured by Cerarica NODA Co., Ltd.): 5.3 parts
Europium complex represented by Chemical formula 2 illustrated above: 4.0 parts
Toner 4 was manufactured in the same manner as Toner 1 except that the toner raw materials were changed as specified above.

The toner particle (Toner 4) prepared as described above had a hydroxyl value of 19.7 mgKOH/g, an Mw of 7.960, a Tg of 58.1 degrees C., and a T(½) of 110.7 degrees C.

Manufacturing Example of Toner 5

Polyester resin RN-290 (hydroxyl value of 35.8 mgKOH/g, manufactured by Kao Corporation): 31.6 parts
Polyester resin RLC-16 (hydroxyl value of 16.5 mgKOH/g, manufactured by Kao Corporation): 63.2 parts
Carnauba wax WA-05 (manufactured by Cerarica NODA Co., Ltd.): 5.3 parts Europium complex represented by Chemical formula 2 illustrated above: 4.0 parts Toner 5 was manufactured in the same manner as Toner 1 except that the toner raw materials were changed as specified above.

The toner particle (Toner 5) prepared as described above had a hydroxyl value of 22.9 mgKOH/g, an Mw of 9.520, a Tg of 58.0 degrees C., and a T(½) of 111.6 degrees C.

Manufacturing Example of Toner 6

Polyester resin RN-290 (hydroxyl value of 35.8 mgKOH/g, manufactured by Kao Corporation): 15.8 parts
Polyester resin RLC-16 (hydroxyl value of 16.5 mgKOH/g, manufactured by Kao Corporation): 52.6 parts
Polyester resin RN-306 (hydroxyl value of 39.5 mgKOH/g, manufactured by Kao Corporation): 26.3 parts
Carnauba wax WA-05 (manufactured by Cerarica NODA Co., Ltd.): 5.3 parts
Europium complex represented by Chemical formula 2 illustrated above: 4.0 parts Toner 6 was manufactured in the same manner as Toner 1 except that the toner raw materials were changed as specified above.

The toner particle (Toner 6) prepared as described above had a hydroxyl value of 26.1 mgKOH/g, an Mw of 8.690, a Tg of 57.7 degrees C., and a T(½) of 114.8 degrees C.

Manufacturing Example of Toner 7

Polyester resin RN-290 (hydroxyl value of 35.8 mgKOH/g, manufactured by Kao Corporation): 52.6 parts
Polyester resin RLC-16 (hydroxyl value of 16.5 mgKOH/g, manufactured by Kao Corporation): 42.1 parts
Carnauba wax WA-05 (manufactured by Cerarica NODA Co., Ltd.): 5.3 parts
Europium complex represented by Chemical formula 2 illustrated above: 4.0 parts Toner 7 was manufactured in the same manner as Toner 1 except that the toner raw materials were changed as specified above.

The toner particle (Toner 7) prepared as described above had a hydroxyl value of 27.2 mgKOH/g, an Mw of 10.240, a Tg of 57.1 degrees C., and a T(½) of 114.1 degrees C.

Manufacturing Example of Toner 8

Polyester resin RN-290 (hydroxyl value of 35.8 mgKOH/g, manufactured by Kao Corporation): 94.7 parts
Carnauba wax WA-05 (manufactured by Cerarica NODA Co., Ltd.): 5.3 parts
Europium complex represented by Chemical formula 2 illustrated above: 4.0 parts Toner 8 was manufactured in the same manner as Toner 1 except that the toner raw materials were changed as specified above.

The toner particle (Toner 8) prepared as described above had a hydroxyl value of 35.8 mgKOH/g, an Mw of 48.606, a Tg of 58.4 degrees C., and a T(½) of 128.6 degrees C.

Manufacturing Example of Toner 9

Polyester resin RN-263 (hydroxyl value of 49 mgKOH/g, manufactured by Kao Corporation): 84.2 parts
Polyester resin RN-306 (hydroxyl value of 39.5 mgKOH/g, manufactured by Kao Corporation): 10.5 parts
Carnauba wax WA-05 (manufactured by Cerarica NODA Co., Ltd.): 5.3 parts
Europium complex represented by Chemical formula 2 illustrated above: 4.0 parts Toner 9 was manufactured in the same manner as Toner 1 except that the toner raw materials were changed as specified above.

The toner particle (Toner 9) prepared as described above had a hydroxyl value of 48.0 mgKOH/g, an Mw of 9.230, a Tg of 56.5 degrees C., and a T(½) of 99.1 degrees C.

Manufacturing Example of Toner 10

Polyester resin RN-290 (hydroxyl value of 35.8 mgKOH/g, manufactured by Kao Corporation): 15.8 parts
Polyester resin RN-306 (hydroxyl value of 39.5 mgKOH/g, manufactured by Kao Corporation): 78.9 parts
Carnauba wax WA-05 (manufactured by Cerarica NODA Co., Ltd.): 5.3 parts
Europium complex represented by the following Chemical formula 3: 4.0 parts Chemical formula 3

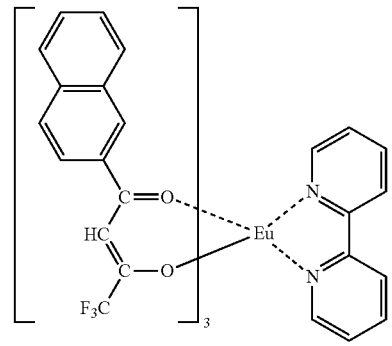

The europium complex represented by the Chemical formula 3 illustrated above was obtained by the method disclosed in JP-2002-173622-A.

Toner 10 was manufactured in the same manner as Toner 1 except that the toner raw materials were changed as specified above.

The toner particle (Toner 10) prepared as described above had a hydroxyl value of 38.9 mgKOH/g, an Mw of 12.301, a Tg of 56.4 degrees C., and a T(½) of 107.0 degrees C.

Manufacturing Example of Toner 11

Polyester resin RN-290 (hydroxyl value of 35.8 mgKOH/g, manufactured by Kao Corporation): 15.8 parts
Polyester resin RN-306 (hydroxyl value of 39.5 mgKOH/g, manufactured by Kao Corporation): 78.9 parts
Carnauba wax WA-05 (manufactured by Cerarica NODA Co., Ltd.): 5.3 parts
Europium complex represented by the following Chemical formula 4: 4.0 parts Chemical formula 4

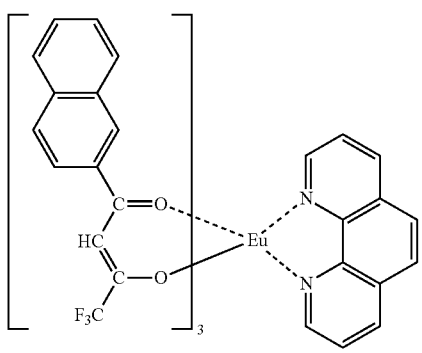

The europium complex represented by the Chemical formula 4 illustrated above was obtained by the method disclosed in JP-2002-173622-A.

Toner 11 was manufactured in the same manner as Toner 1 except that the toner raw materials were changed as specified above.

The toner particle (Toner 11) prepared as described above had a hydroxyl value of 38.9 mgKOH/g, an Mw of 11.620, a Tg of 56.7 degrees C., and a T(½) of 107.1 degrees C.

Manufacturing Example of Toner 12

Polyester resin RN-290 (hydroxyl value of 35.8 mgKOH/g, manufactured by Kao Corporation): 15.8 parts
Polyester resin RN-306 (hydroxyl value of 39.5 mgKOH/g, manufactured by Kao Corporation): 78.9 parts
Carnauba wax WA-05 (manufactured by Cerarica NODA Co., Ltd.): 5.3 parts
Europium complex represented by the following Chemical formula 5: 4.0 parts Chemical formula 5

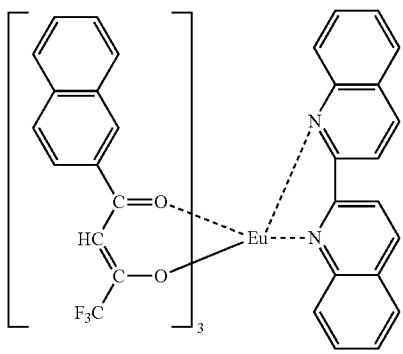

The europium complex represented by the Chemical formula 5 illustrated above was obtained by the method disclosed in JP-2002-173622-A.

Toner 12 was manufactured in the same manner as Toner 1 except that the toner raw materials were changed as specified above.

The toner particle (Toner 12) prepared as described above had a hydroxyl value of 38.9 mgKOH/g, an Mw of 11.400, a Tg of 57.0 degrees C., and a T(½) of 107.6 degrees C.

Manufacturing Example of Toner 13

Polyester resin RN-290 (hydroxyl value of 35.8 mgKOH/g, manufactured by Kao Corporation): 15.8 parts
Polyester resin RN-306 (hydroxyl value of 39.5 mgKOH/g, manufactured by Kao Corporation): 78.9 parts
Carnauba wax WA-05 (manufactured by Cerarica NODA Co., Ltd.): 5.3 parts
Europium complex represented by the following Chemical formula 6: 4.0 parts Chemical formula 6

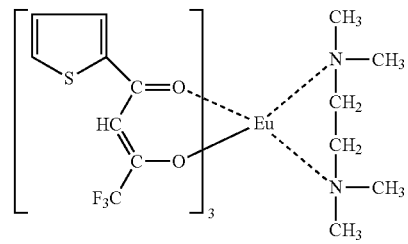

The europium complex represented by Chemical formula 6 illustrated above was obtained by the method disclosed in JP-2002-173622-A.

Toner 13 was manufactured in the same manner as Toner 1 except that the toner raw materials were changed as specified above.

The toner particle (Toner 13) prepared as described above had a hydroxyl value of 38.9 mgKOH/g, a Mw of 11.280, a Tg of 56.4 degrees C., and a T(½) of 107.0 degrees C.

Manufacturing of Two Component Developer
Manufacturing of Carrier
Silicone resin (Organo straight silicone): 100 parts
Toluene: 100 parts
γ-(2-aminoethyl)aminopropyl trimethoxy silane: 5 parts
Carbon Black: 10 parts The mixture specified above was dispersed by a Homomixer for 20 minutes to prepare a liquid for forming a coating layer. This liquid for forming a coating layer was applied to Mn ferrite particles having a weight average particle diameter of 35 µm as core material by a fluid bed type coating device while controlling the temperature in the fluid tank at 70 degrees C. followed by drying in such a manner that the average layer thickness of the coated layer on the surface of the core material was 0.20 µm. The thus-obtained carrier was baked in an electric furnace at 180 degrees C. for two hours to obtain Carrier A.

Manufacturing of Two Component Developer

Each of the manufactured toners and Carrier A were uniformly mixed and charged by a TURBULA® mixer (manufactured by Willy A. Bachofen AG) at 48 rpm for five minutes to manufacture each two-component developer. The mixing ratio of the toner and the carrier was adjusted to the toner concentration of 4 percent by mass of initial developer in the evaluation machine.

Evaluation

The two-component developers produced from Toners 1 to 13 were evaluated based on the following evaluation method. The results are shown in Tables 1-1, 1-2, and 1-3.

Fluorescence

The two-component developers prepared from Toners 1 to 13 were charged into the developing unit of Imagio Neo C350 (manufactured by Ricoh Company, Ltd.) followed by adjustment in such a manner that the adhesion amount was 0.65 mg/cm³, at which suitable coloring property was obtained. Thereafter, a solid image was output to POD gloss paper (manufactured by Oji Paper Co., Ltd.). The adhesion amount means the amount of toner adhering to the transfer sheet.

With respect to this image, the L* value measured with the m1 light source and the L* value measured with the m2 light source were determined. Thereafter, the value of (L* value measured with m2 light source)−(L* value measured with m1 light source) was defined as the index value ΔL*, which was evaluated according to the following evaluation criteria. The larger ΔL*, the higher the fluorescence. The grade C means not allowable.

The measuring values were obtained by measuring the color under the condition of colorimetric status T with a spectral densitometer X-riteEXACT (manufactured by X-Rite Inc.).

Evaluation Criteria
A: Greater than 0.2
B: Greater than 0.1 to 0.2
C: 0.1 or less High Temperature and High Humidity Storage Stability 0.5 g of toner was weighed and charged in a centrifuge tube and stored for 2 weeks under the conditions of a temperature of 40 degrees C. and a relative humidity of 70 percent. Subsequent to sieving with a mesh opening of 106 μm, the amount of the loose aggregate remaining on the mesh was measured.

Based on the value of the loose aggregate amount, the high temperature and high humidity storage stability was evaluated according to the following criteria:

The grade C means not allowable.
Evaluation Criteria
A: 200 mg/g or less
B; Greater than 200 to 250 mg/g
C: Greater than 250 mg/g Gloss The two-component developers prepared from Toners 1 to 13 were charged into the developing unit of MP C3503 (manufactured by Ricoh Company, Ltd.) followed by adjustment in such a manner that the adhesion amount was 0.65 mg/cm³, at which suitable coloring property was obtained. Thereafter, a solid image was output to POD gloss paper (manufactured by Oji Paper Co., Ltd.). The adhesion amount means the amount of toner adhering to the transfer sheet.

With respect to this image, gloss feeling was evaluated based on the following criteria based on sensory evaluation by visual observation. The grade C means not allowable.

Evaluation Criteria
A: No gloss difference between image part and non-image part
B: Gloss difference between the image portion and the non-image portion was felt depending on the viewing angle
C: Gloss difference between the image portion and the non-image portion was felt irrespective of the viewing angle Chargeability Regarding the two-component developer prepared from Toners 1 to 13, the charge amount was measured using a blow-off device TB-200 (manufactured by Toshiba Chemical Co., Ltd.). Based on these measuring values, chargeability was evaluated according to the following criteria. The grade C means not allowable.

Evaluation Criteria
A: Greater than 27 (−μC/g)
B: Greater than 23 to 27 (−μC/g)
C: 23 (−μC/g) or less

TABLE 1-1

| | | | Example 1 | Comparative Example 1 | Example 2 | Comparative Example 2 | Example 3 |
|---|---|---|---|---|---|---|---|
| | Toner No. | | 1 | 2 | 3 | 4 | 5 |
| Prescription amount (parts by mass) | Polyester resins | RN-290 | 15.8 | 15.8 | 15.8 | 15.8 | 31.6 |
| | | RN-263 | — | 78.9 | — | — | — |
| | | RLC-16 | — | — | — | 78.9 | 63.2 |
| | | RN-306 | 78.9 | — | — | — | — |
| | | RN-300 | — | — | 78.9 | — | — |
| | Carnauba wax | WA-05 | 5.3 | 5.3 | 5.3 | 5.3 | 5.3 |
| | Europium complex | Chemical formula 2 | 4.0 | 4.0 | 4.0 | 4.0 | 4.0 |
| | | Chemical formula 3 | — | — | — | — | — |
| | | Chemical formula 4 | — | — | — | — | — |
| | | Chemical formula 5 | — | — | — | — | — |
| | | Chemical formula 6 | — | — | — | — | — |
| Evaluation result | Hydroxyl value | | 38.9 | 46.8 | 31.8 | 19.7 | 22.9 |
| | Fluorescence ΔL* | | A | A | A | B | B |
| | Chargeability | | A | B | A | C | B |
| | High temperature and high humidity storage stability | | A | C | A | A | A |
| | Gloss feeling | | A | A | A | A | A |

TABLE 1-2

| | | | Example 4 | Example 5 | Example 6 | Comparative Example 3 | Comparative Example 4 |
|---|---|---|---|---|---|---|---|
| | Toner No. | | 6 | 7 | 8 | 9 | 10 |
| Prescription amount (parts by mass) | Polyester resins | RN-290 | 15.8 | 52.6 | 94.7 | — | 15.8 |
| | | RN-263 | — | — | — | 84.2 | — |
| | | RLC-16 | 52.6 | 42.1 | — | — | — |
| | | RN-306 | 26.3 | — | — | 10.5 | 78.9 |
| | | RN-300 | — | — | — | — | — |
| | Carnauba wax | WA-05 | 5.3 | 5.3 | 5.3 | 5.3 | 5.3 |
| | Europium complex | Chemical formula 2 | 4.0 | 4.0 | 4.0 | 4.0 | — |
| | | Chemical formula 3 | — | — | — | — | 4.0 |
| | | Chemical formula 4 | — | — | — | — | — |
| | | Chemical formula 5 | — | — | — | — | — |
| | | Chemical formula 6 | — | — | — | — | — |
| Evaluation result | Hydroxyl value | | 26.1 | 27.2 | 35.8 | 48.0 | 38.9 |
| | Fluorescence ΔL* | | A | A | A | A | C |
| | Chargeability | | B | B | A | A | A |
| | High temperature and high humidity storage stability | | A | A | A | C | C |
| | Gloss feeling | | A | A | B | C | A |

TABLE 1-3

| | | | Comparative Example 5 | Comparative Example 6 | Comparative Example 7 |
|---|---|---|---|---|---|
| | Toner No. | | 11 | 12 | 13 |
| Prescription amount (parts by mass) | Polyester resins | RN-290 | 15.8 | 15.8 | 15.8 |
| | | RN-263 | — | — | — |
| | | RLC-16 | — | — | — |
| | | RN-306 | 78.9 | 78.9 | 78.9 |
| | | RN-300 | — | — | — |
| | Carnauba wax | WA-05 | 5.3 | 5.3 | 5.3 |
| | Europium complex | Chemical formula 2 | — | — | — |
| | | Chemical formula 3 | — | — | — |
| | | Chemical formula 4 | 4.0 | — | — |
| | | Chemical formula 5 | — | 4.0 | — |
| | | Chemical formula 6 | — | — | 4.0 |
| Evaluation result | Hydroxyl value | | 38.9 | 38.9 | 38.9 |
| | Fluorescence ΔL* | | C | B | B |
| | Chargeability | | A | C | C |
| | High temperature and high humidity storage stability | | B | C | B |
| | Gloss feeling | | A | A | A |

Judging from the results, the toners of Examples realized fluorescence and practicality beyond typical process colors. In contrast, the toners of Comparative Examples had insufficient fluorescence (Comparative Examples 4 and 5), shortage of chargeability (Comparative Example 2, 6, and 7), poor high-temperature and high-humidity storage stability (Comparative Example 1, 3, 4, and 6), and poor gloss feeling (Comparative Example 3), all of which was inferior in performance to the toner of Examples.

Aspects of the present disclosure are, for example, as follows.

1. The toner contains the europium complex represented by the following Chemical formula 1 and has a hydroxyl value of from 20 to 40 mgKOH/g

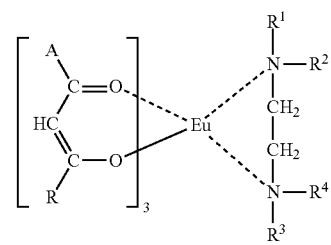

Chemical formula 1

In Chemical formula 1, A represents non-substituted 2-naphthyl group or 2-naphthyl group having a substitution group selected from the group consisting of an alkyl group, an alkoxy group, and a halogen, R represents a fluoroalkyl group having one to three carbon atoms or a methyl group, and $R^1$, $R^2$, $R^3$, and $R^4$ each, independently represent hydrogen atoms, alkyl groups, or aryl groups.

2. The toner according to 1 mentioned above, wherein the hydroxyl value is from 30 to 40 mgKOH/g.
3. The toner according to 1 or 2 mentioned above, wherein the toner has a portion soluble in tetrahydrofuran (THF) that has a weight average molecular of from 6,000 to 12,000.
4. The toner according to 3 mentioned above, wherein the toner has a portion soluble in tetrahydrofuran (THF) that has a weight average molecular weight of from 7,000 to 10,000.
5. The toner according to any one of 1 to 4 mentioned above, wherein the half efflux temperature of the toner is from 105 to 120 degrees C.
6. The toner according to any one of 1 to 5 mentioned above, wherein the glass transition temperature of the toner is from 50 to 60 degrees C.
7. The toner according to any one of 1 to 6 mentioned above, wherein the europium complex is represented by the following Chemical formula 2.

Chemical formula 2

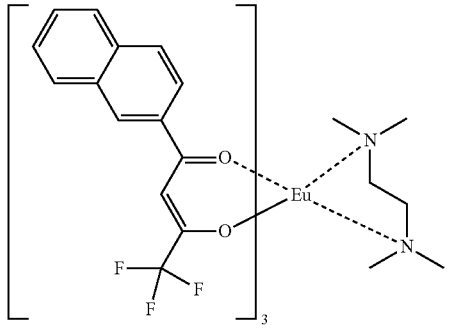

8. The toner according to any one of 1 to 7 mentioned above includes a binder resin.
9. The toner according to 8, wherein the binder resin contains a polyester resin.
10. The toner according to 8 or 9 mentioned above, wherein the content of the europium complex is from 0.5 to 10.0 parts by mass to 100 parts by mass of the binder resin in the toner.
11. The toner according to any one of 8 to 10 mentioned above further includes a releasing agent, wherein the content of the europium complex is from 0.5 to 10.0 parts by mass to 100 parts of the total content of the binder resin and the releasing agent in the toner.
12. An image forming apparatus includes a latent electrostatic image bearer, a latent electrostatic image forming device to form a latent electrostatic image on the latent electrostatic image bearer, a developing device to develop the latent electrostatic image on the latent electrostatic image bearer with the toner of any one of 1 to 11 mentioned above form a toner image, a transfer device to transfer the toner image onto the surface of a recording medium, and a fixing device to fix the toner image on the surface of the recording medium.
13. An image forming method includes forming a latent electrostatic image on a latent electrostatic image bearer, developing the latent electrostatic image formed on the latent electrostatic image bearer with the toner of any one of 1 to 11 mentioned above to form a toner image, transferring the toner image formed on the latent electrostatic image bearer to the surface of a recording medium, and fixing the toner image on the surface of the recording medium.
14. A toner accommodating unit includes the toner of any one of 1 to 11 mentioned above.

According to the present disclosure, an invisible UV light emission toner having fluorescence under ultraviolet irradiation is provided, which can reproduce color not reproducible by typical process colors.

The above-described embodiments are illustrative and do not limit the present invention. Thus, numerous additional modifications and variations are possible in light of the above teachings. For example, elements and/or features of different illustrative embodiments may be combined with each other and/or substituted for each other within the scope of the present invention.

What is claimed is:

1. A toner comprising:
a europium complex represented by the following Chemical formula 1

Chemical formula 1

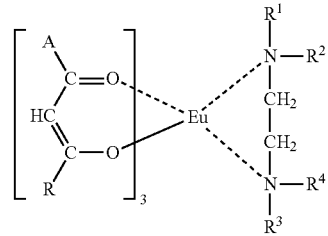

where A represents 2-naphthyl group, 2-naphthyl group having a substitution group selected from the group consisting of an alkyl group, an alkoxy group, and a halogen, R represents a fluoroalkyl group having one to three carbon atoms or a methyl group, and $R^1$, $R^2$, $R^3$, and $R^4$ each, independently represent hydrogen atoms, alkyl groups, or aryl groups, wherein the toner has a hydroxyl value of from 20 to 40 mgKOH/g.

2. The toner according to claim 1, wherein the hydroxyl value is from 30 to 40 mgKOH/g.
3. The toner according to claim 1, wherein the toner has a portion soluble in tetrahydrofuran (THF) that has a weight average molecular of from 6,000 to 12,000.
4. The toner according to claim 1, wherein the toner has a half efflux temperature of from 105 to 120 degrees C.
5. The toner according to claim 1, wherein the europium complex is represented by the following Chemical formula 2:

Chemical formula 2

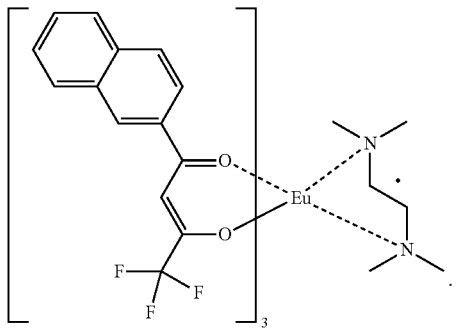

6. An image forming apparatus comprising:
a latent electrostatic image bearer;
a latent electrostatic image forming device configured to form a latent electrostatic image on the latent electrostatic image bearer;
a developing device provided with the toner of claim 1 and configured to develop the latent electrostatic image on the latent electrostatic image bearer with the toner of claim 1 to form a toner image;
a transfer device configured to transfer the toner image onto a surface of a recording medium; and
a fixing device configured to fix the toner image on the surface of the recording medium.

7. An image forming method comprising:
forming a latent electrostatic image on a latent electrostatic image bearer;
developing the latent electrostatic image formed onto the latent electrostatic image bearer with the toner of claim 1 to form a toner image;
transferring the toner image formed on the latent electrostatic image bearer to a surface of a recording medium; and
fixing the toner image on the surface of the recording medium.

8. A toner accommodating unit comprising:
the toner of claim 1.

* * * * *